(12) United States Patent
Herrera (10) Patent No.: US 9,820,750 B2
(45) Date of Patent: Nov. 21, 2017

(54) METHOD FOR DYNAMIC REGULATIONS (COUNTER PULSATION) OF THE VENOUS RETURN TO THE HEART FOR THE TREATMENT OF PATIENTS WITH HEART FAILURE

(71) Applicant: Jose E. Herrera, Porlamar (VE)

(72) Inventor: Jose E. Herrera, Porlamar (VE)

( * ) Notice: Subject to any disclaimer, the term of this patent is extended or adjusted under 35 U.S.C. 154(b) by 206 days.

(21) Appl. No.: 14/635,653

(22) Filed: Mar. 2, 2015

(65) Prior Publication Data

US 2015/0265285 A1 Sep. 24, 2015

Related U.S. Application Data

(60) Division of application No. 12/801,813, filed on Jun. 28, 2010, now Pat. No. 8,968,239, which is a
(Continued)

(51) Int. Cl.
*A61M 31/00* (2006.01)
*A61M 37/00* (2006.01)
(Continued)

(52) U.S. Cl.
CPC .. *A61B 17/12136* (2013.01); *A61B 17/12031* (2013.01); *A61B 17/12036* (2013.01);
(Continued)

(58) Field of Classification Search
CPC .... A61B 17/12136; A61B 2017/12054; A61B 17/12036; A61M 2025/1052;
(Continued)

(56) References Cited

U.S. PATENT DOCUMENTS

| | | | | |
|---|---|---|---|---|
| 6,033,379 A | * | 3/2000 | Barra | A61M 25/10 604/103.11 |
| 7,713,282 B2 | * | 5/2010 | Frazier | A61B 17/0057 606/200 |

(Continued)

*Primary Examiner* — Rebecca E Eisenberg
(74) *Attorney, Agent, or Firm* — Ference & Associates LLC (57) ABSTRACT

This invention relates to a method that comprises the introduction of a catheter via left subclavian vein, advancing into the right atrium and then positioning it in the inferior vena cava, just at the cava-diaphragm junction, where it is anchored at its extreme; and thereafter an external inflation of a balloon positioned in said catheter takes place through a physiological solution to reach a diameter corresponding to half the diameter of the inferior vena cava, resulting in hemi-occlusion in the expiration phase (breath-out) and total occlusion for a short period during the inspiration phase (breath-in), regulating (normalizing) the venous return and decreasing the cardiac volume overload, as a treatment for heart failure. The invention also comprises hydromechanics devices to normalize the venous return in the circulatory system. Said venous return is increased in 90% of patients with heart failure. In particular, it refers to a combined catheter with an inflatable balloon, producing said balloon a cyclical occlusion of the inferior vena cava, proximal to the right atrium (RA), which comprises of means for its fixation within said vein, as well as the capacity of modifying the volume in response to the requirements of the patient. This device is implanted for an extended period of more than three months. The final objective is to treat and stop the progression of heart failure.

16 Claims, 8 Drawing Sheets

Related U.S. Application Data continuation-in-part of application No. 12/202,617, filed on Sep. 2, 2008, now abandoned.

(51) Int. Cl.
*A61M 29/00* (2006.01)
*A61B 17/12* (2006.01)
*A61M 25/04* (2006.01)
*A61M 25/10* (2013.01)
*A61M 25/00* (2006.01)

(52) U.S. Cl.
CPC ....... *A61B 17/12109* (2013.01); *A61M 25/04* (2013.01); *A61M 25/1002* (2013.01); *A61B 2017/12054* (2013.01); *A61M 2025/0096* (2013.01); *A61M 2025/1052* (2013.01); *A61M 2025/1086* (2013.01)

(58) Field of Classification Search
CPC .......... A61M 2025/1086; A61M 25/04; A61M 25/1002; A61M 25/10; A61M 2025/1054
See application file for complete search history.

(56) References Cited

U.S. PATENT DOCUMENTS

| | | | | |
|---|---|---|---|---|
| 2003/0009095 A1* | 1/2003 | Skarda | ............... | A61B 18/1492 600/374 |
| 2008/0051707 A1* | 2/2008 | Phan | .................. | A61B 17/8855 604/108 |
| 2008/0071339 A1* | 3/2008 | Stalker | .................... | A61N 1/05 607/119 |

* cited by examiner

METHOD FOR DYNAMIC REGULATIONS (COUNTER PULSATION) OF THE VENOUS RETURN TO THE HEART FOR THE TREATMENT OF PATIENTS WITH HEART FAILURE

CROSS REFERENCE TO RELATED APPLICATIONS

This application is a divisional application of co-pending U.S. patent application Ser. No. 12/801,813, filed Jun. 28, 2010, which in turn is a continuation-in-part of U.S. patent application Ser. No. 12/202,617, filed Sep. 2, 2008; the contents of each of these prior applications are hereby incorporated by reference as if set forth in their entirety.

BACKGROUND

It has been known within the field of the specialty that heart failure is a result of the increase of the venous return which causes volume overload and severe pulmonary congestion; so that the decrease of venous return (normalization) is crucial in the improvements of the symptoms of said pulmonary congestion and heart failure. In early attempts to solve the problem, bloodletting and tourniquet in the lower extremities were used as a means to normalize venous return, to improve the pulmonary congestion.

In later years, the use of mercurial diuretics started, then stronger ASA diuretics, furosemide and bumetanide helped to rapidly decrease the venous return, with improvements of the heart failure symptoms; however, there were deleterious effects on the renal function, such as hydro-electrolytic disorders and renal damages.

The persistence of the problem of the increased venous return led to the use of nitride and nitrates, which produce a venous dilatation, causing a reduction on the venous return, improving the symptoms for a short period of time; but the inherent intolerance in this type of medication causes the loss of the effect in a few months, with the additional inconvenience of associated headaches as side effects, as it was observed in a large percentage of patients, resulting in risks of the use of these medicines during extended periods of time.

After the introduction of receptor blockers of aldosterone (spironolactona), hydro saline retention was minimized, as well as venous return; however, the receptor blockers produced serious side effects.

Later on, a new pharmacological alternative was introduced in the form of drugs that block the formation of angiotensin, which produced the decrease of venous return, improving the quality of life of a patient with heart failure.

Subsequently, the use of beta blockers of the last generation type (carvediol) was advocated, and the same produced significant benefits in patients with heart failure, being a treatment choice for a high number of patients with heart failure.

With the advent of receptor blockers (V1-V2) of the neuro-hormonal arginine-vasopressin axis (type Tolvaptan, Conivaptan), a reducer of corporal water, decrease of venous return and improvement of pulmonary congestion is achieved for a very short period of time and at an extremely high price.

The proposal to use stem cells for the treatment of heart failure was assessed at the Annual Meeting of The American Heart Association 2007. It was considered then that this technique caused little improvement in the ejection fraction of the left ventricle; and better results are obtained only when the venous return is diminished through diuretic administration.

There is no similar method to that described in this invention to treat and improve heart failure. At a device level, there are only inflatable balloons for temporary use during an invasive procedure as used in U.S. Patent No. 2003/0208232 to Blaeser et al. (Blaeser) and in U.S. Patent No. 2006/0074399 to Bates (Bates).

It is evident that effective management of the venous return is very important in improving the left ventricle function.

Lastly, in those extreme cases where known medical therapeutic measures fail, mechanical methods are used to normalize the venous return via extraction of corporal water, as the dialysis and ultra-filtration, which, although they enable good effects, in the symptoms of a congestive heart failure, this is for a short period; and the body water come backs to a state of increased venous return, causing the symptoms of pulmonary congestion and low cardiac output to reappear.

OBJECTIVES OF THE INVENTION

One of the objectives of the invention is to solve in an efficient and effective way the above outlined problems through a method of regularization of the venous return by means of hydraulic devices, in patients suffering congestive heart failure.

Another objective of the invention is to provide said regularization using a device that includes a two-way catheter carrying an inflatable balloon, adjustable in volume, comprising several external slots, so that in case of prolonged total occlusion of the inferior vena cava (laughing, coughing), these will allow the passage of venous return, as an alleviating channel to avoid cardio-circulatory collapse. Said balloon is filled from the outside, to the required setting, with a saline solution, through which an occlusion of the inferior vena cave is formed during the inspiration phase (breath in.)

An additional objective of the invention, once the catheter/balloon is placed, anchored, and inflated in the proximal portion of the inferior vena cava, is to produce an instantaneous dynamic cyclic occlusion depending on the respiratory phases, thereby obtaining the normalization of the flow running from the inferior vena cava toward the right atrium (RA).

DESCRIPTION OF THE INVENTION

The present invention is intended, as previously mentioned, to provide a method and a device for the mechanical regulation of increased venous return (normalization) in patients with congestive heart failure; and it is based on the use of a catheter carrying an adjustable inflatable balloon, exhibiting eight (8) external slots. Said catheter and balloon are percutaneously inserted, via left subclavian vein, continuing its pass through the right atrium and carried to the proximal portion of the inferior vena cava, in which it is anchored to the right sidewall, so that the balloon stays very close to the inferior vena cava outlet, in which the inspiratory collapse is maximal. After that, the balloon is inflated to a point to be determined for each patient, according to the needs of occlusion of said vein. The inflated balloon produces an instant and cyclical occlusion, according to the continuous succession of inspiratory collapses and expirations, thereby providing a flow regulation that runs from the inferior vena cava into the right atrium.

In this way, the load conditions of the right atrium, right ventricle and left ventricle are decreased. This situation is repeated in each inspiration (breath-in), preventing an increase of the flow rate that normally occurs in each inspiration, reducing also the flow rate and the filing pressure at the left and right ventricles.

As a result of this normalization of venous return, there is a decrease of pulmonary congestion on the diastolic diameters of both ventricles and an improvement in the left ventricular ejection.

This model of instantaneous and dynamic regulation of the flow has the advantage that the balloon can be easily implanted by an expert; it is possible to modify and adjust it in situ without difficulty, in order to obtain the expected results; and no external power generation is required to operate, since the flow regulation (normalization) is supported by the physiology of the patients when breathing in. Additionally, said device can be removed without difficulties when required, by simply emptying the contents of the balloon from the outside.

The operating mode of the method proposed by this Inventor to regulate the balloon and obtain the appropriate regulatory effect in each case or situation can be explained, in a general form, through the Examples that follow and then through the corresponding illustrative figures attached below:

Example 1

After localizing the patient's inferior vena cava by way of 2D echocardiography, in sub-costal position, in long axis view, its diameter should be measured during expiration (e.g., 2 cm). The collapse is measured during patient inspiration (breath in), normally in the range of 50%, that is, 1 cm diameter reduction for the said case.

Under these conditions, the balloon has to be inflated up to 1 cm to complete 100% occlusion, when inspiration takes place (breath-in.)

Example 2

In the case that the inferior vena cava measures 2 cm and the inspiratory collapse is 40%, the diameter of the vessel decreases to 1.2 cm; therefore, the balloon should be inflated to that same measurement to obtain the desired occlusion of 100% during inspiration, thus achieving a dynamic flow regulation.

At the next stage of expiration, the inferior vena cava returns to its normal diameter, allowing venous return through the remaining area.

Figure 1:
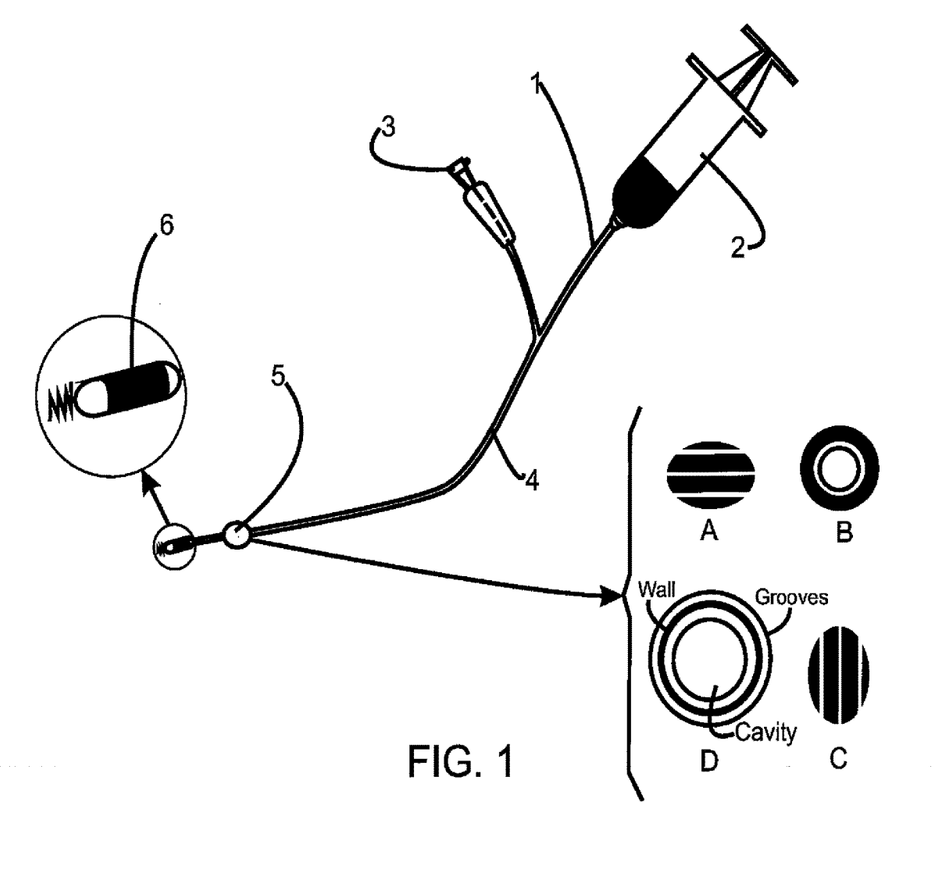
FIG. 1 is a schematic view of the device that includes an inflatable balloon with amplified details of this element at the distal end of the catheter, wherein A is a longitudinal sectional view; B is a cross-sectional view; C is a sagittal view, D is an amplified cross-sectional view of B, E is a cross-sectional external view, and F is an external top view.
Figure 2A:
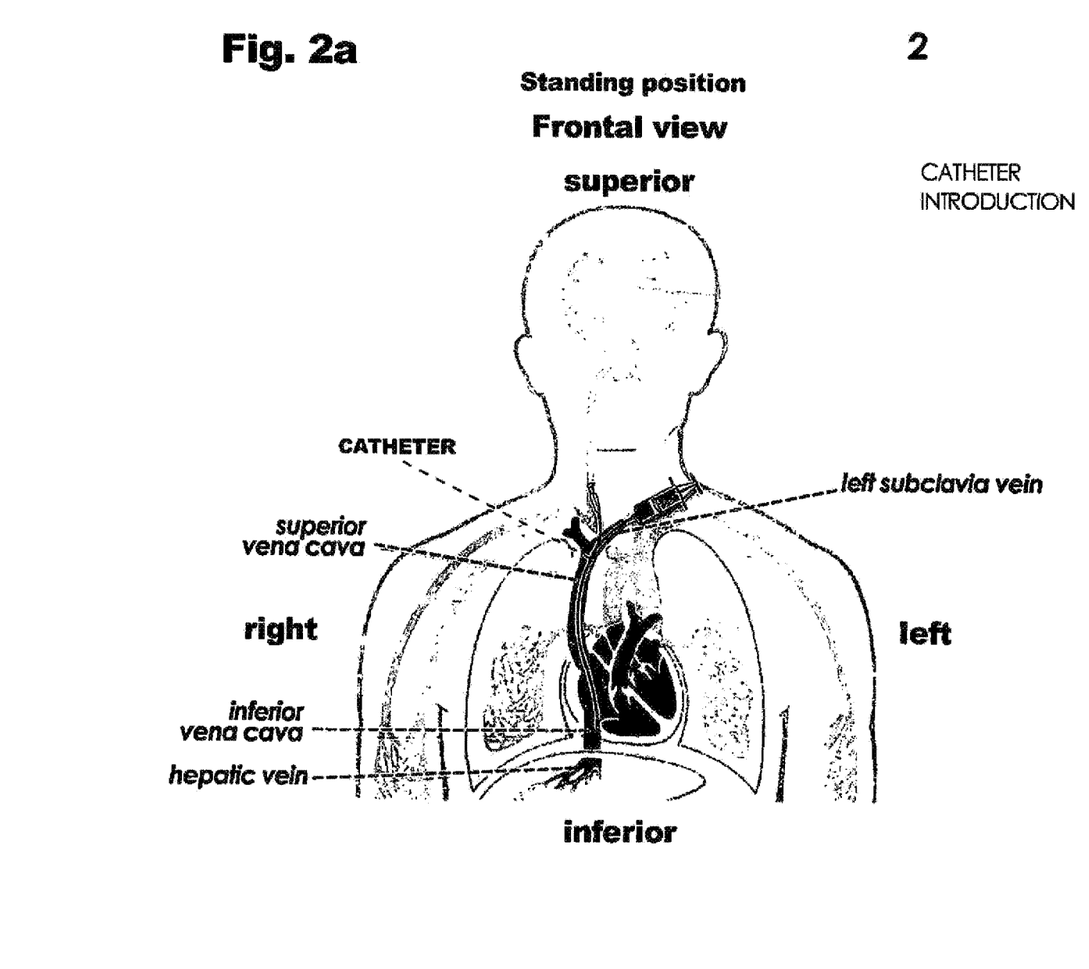
FIG. 2a is a demonstration of the device being implanted in a human body.
Figure 2B:
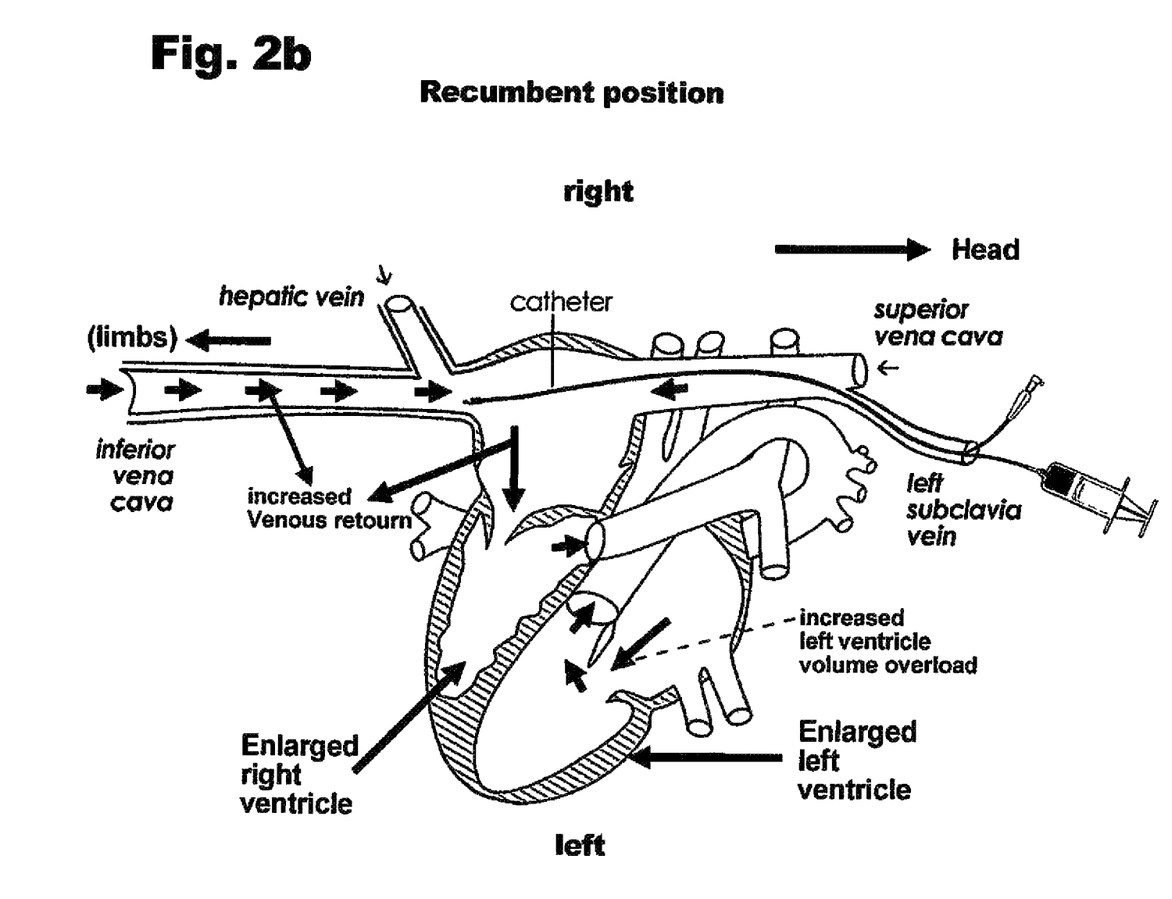
FIG. 2b is an enlarged view of the implantation of the device via the left subclavian vein through the superior vena cava until reaching the inferior vena cava.

Making a detailed description of the above described figures, it can be seen that FIG. 1 is comprised of a catheter (1) with a bifurcation (4) at its proximal end in which one of the branches leads to a cylindrical body (2) provided with an injection embolus (saline or glucose solution) into the interior of the balloon (5); and the other branch is provided with a jacket (3) to pass a probe and act on the distal retractable screw (6) for the anchoring of the catheter to the inferior vena cava. This retractable screw is a conventional element used since 1978 (Hurts, John Willis 19787), the Heart Text Book, page 701. The injection element (2) also features a non-return valve (7) to prevent the regression of the injected liquid into the balloon (5). Said balloon (5), as can be seen in the broken down detail A of FIG. 1, is egg-shaped to ease the flow of the bloodstream further comprising of superficial slots parallel oriented to the longitudinal axis of the inferior vena cava.

The balloon (5) is intended to be inflated with a saline or glucose solution through the catheter in a range from 1 to 2 cm, in its greater diameter, depending on the patient needs. The wall of the balloon has a thickness of 1 mm covered by 8 slots of 305 mm in depth and 1 mm in width. The purpose of these slots is to act as relief of the venous return in the event of a total and prolonged occlusion of the inferior vena cava due to physiological conditions, such as coughing, laughing and evacuating (going to the toilet, etc.)

FIGS. 3a, 3b, 4a, and 4b schematically show how the proposed method of the invention operates assuming a patient with congestive heart failure. In FIG. 3 is seen a portion of the inferior vena cava corresponding to the confluence zone of said vena cava with the hepatic vein, where said vena cava is at the stage of expiration and at a diameter of 2 cm. The balloon (5) (diameter=1 cm) previously inserted in the vena cava, is near the outlet of the hepatic veins, the area of major inspiratory collapse.

Figure 3A:
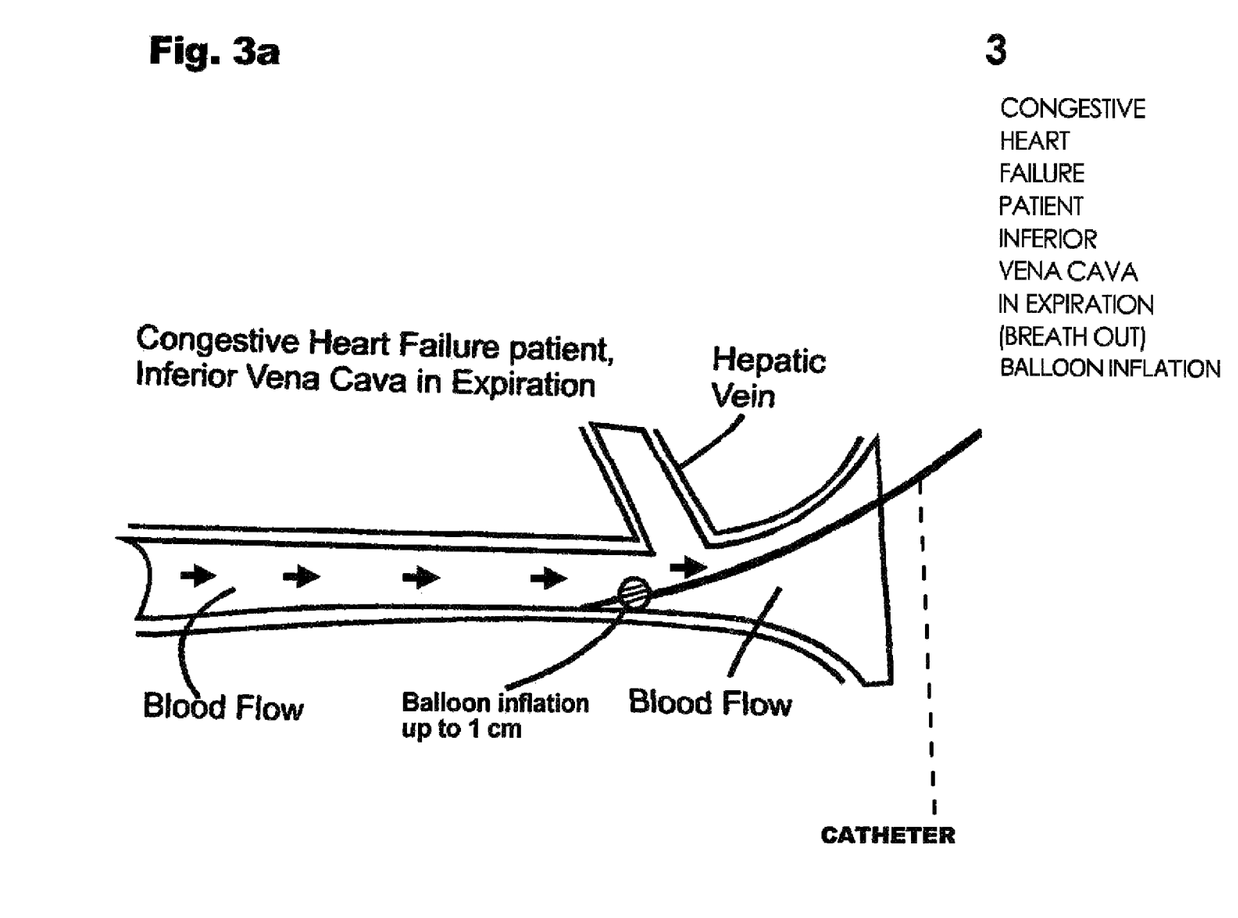
FIG. 3a is an enlarged view of the inferior vena cava in expiration condition with the balloon anchored to that vein.

In the expiration condition, it can be seen that the flow of the bloodstream is essentially affected by minimal restriction.

Figure 3B:
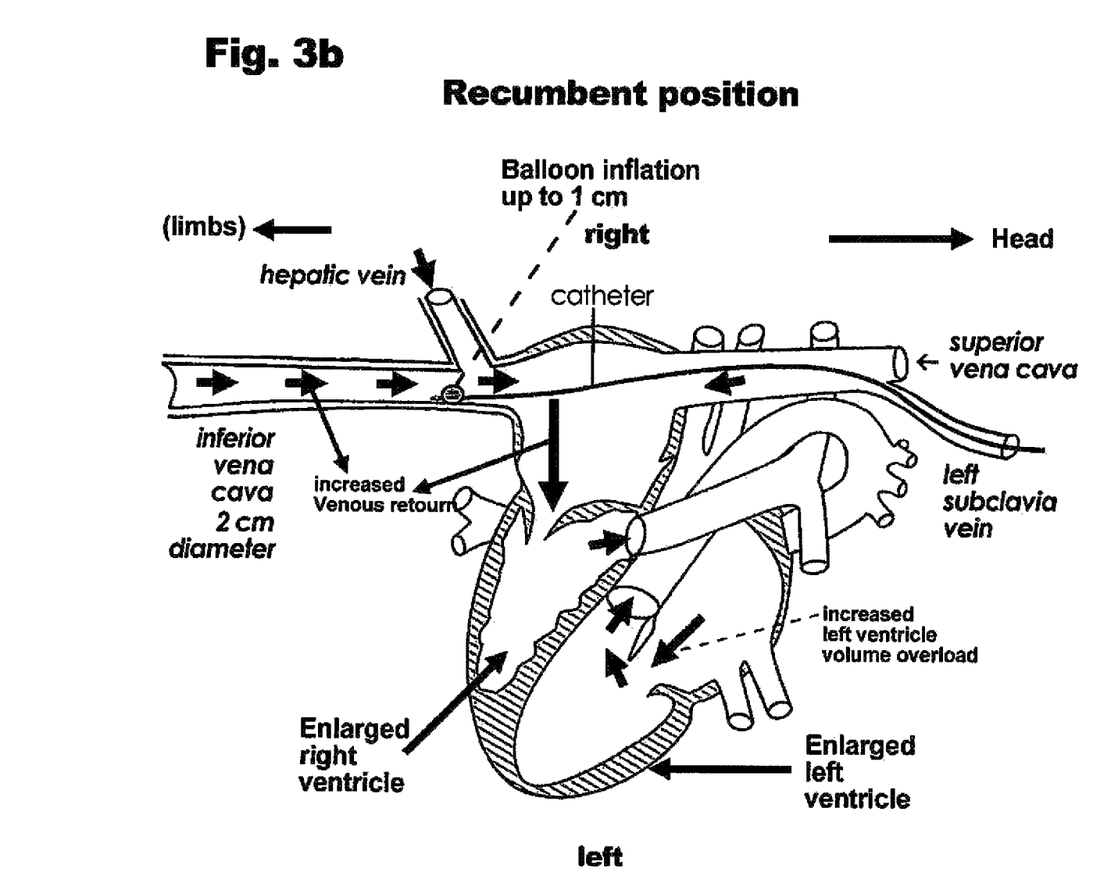
FIG. 3b is a complementary view of FIG. 3a, which includes the human heart in the initial phase of treatment of heart failure (dilated heart).

FIG. 3b is a view of the whole device, including the anatomy of the human heart at the initial stage of the treatment, where the dilated heart due to congestive heart failure (CHF) can be seen.

Figure 4A:
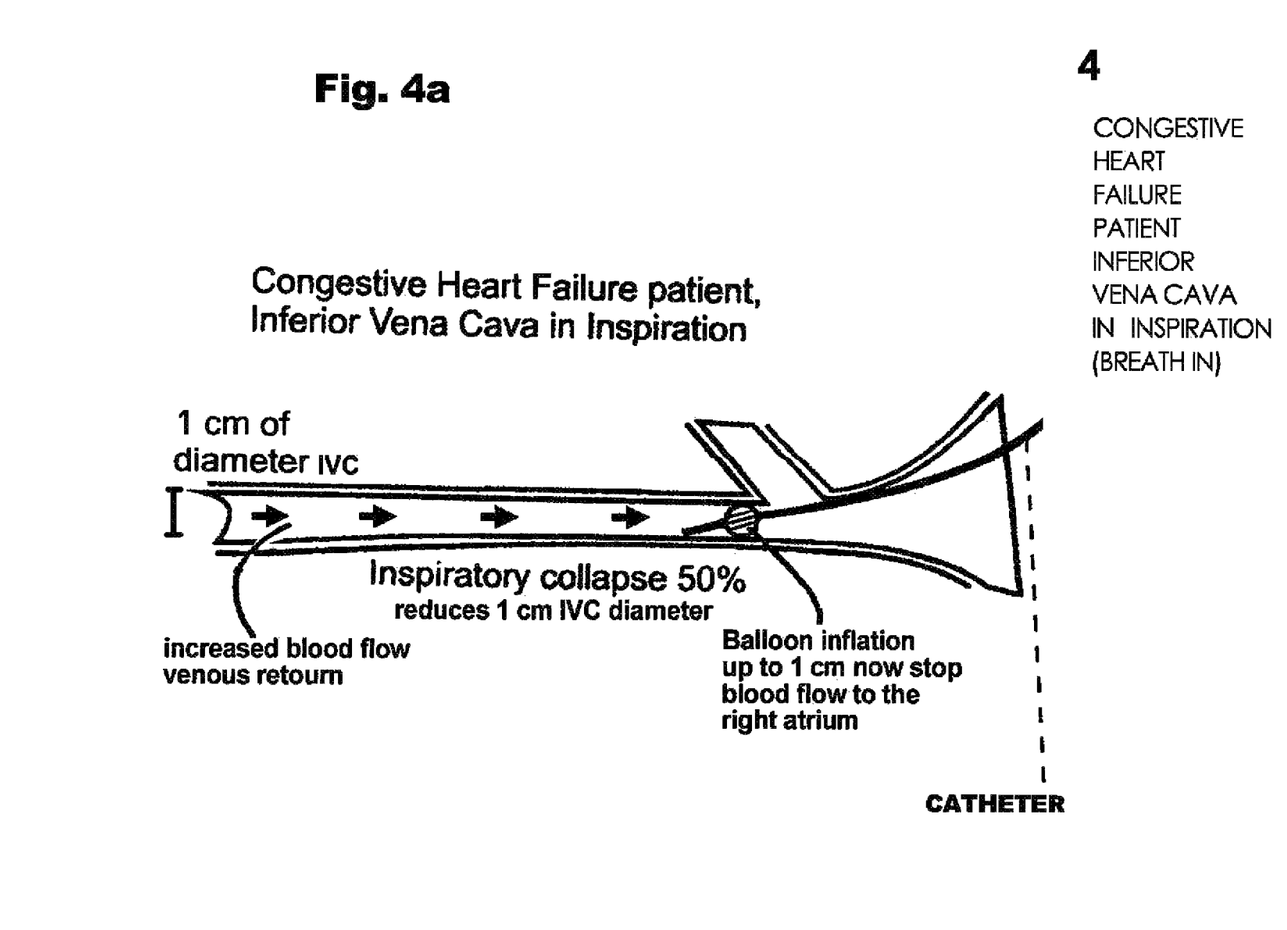
FIG. 4a is a view similar to FIG. 2a, only to indicate the return of the vein to the condition of inspiration.
Figure 4B:
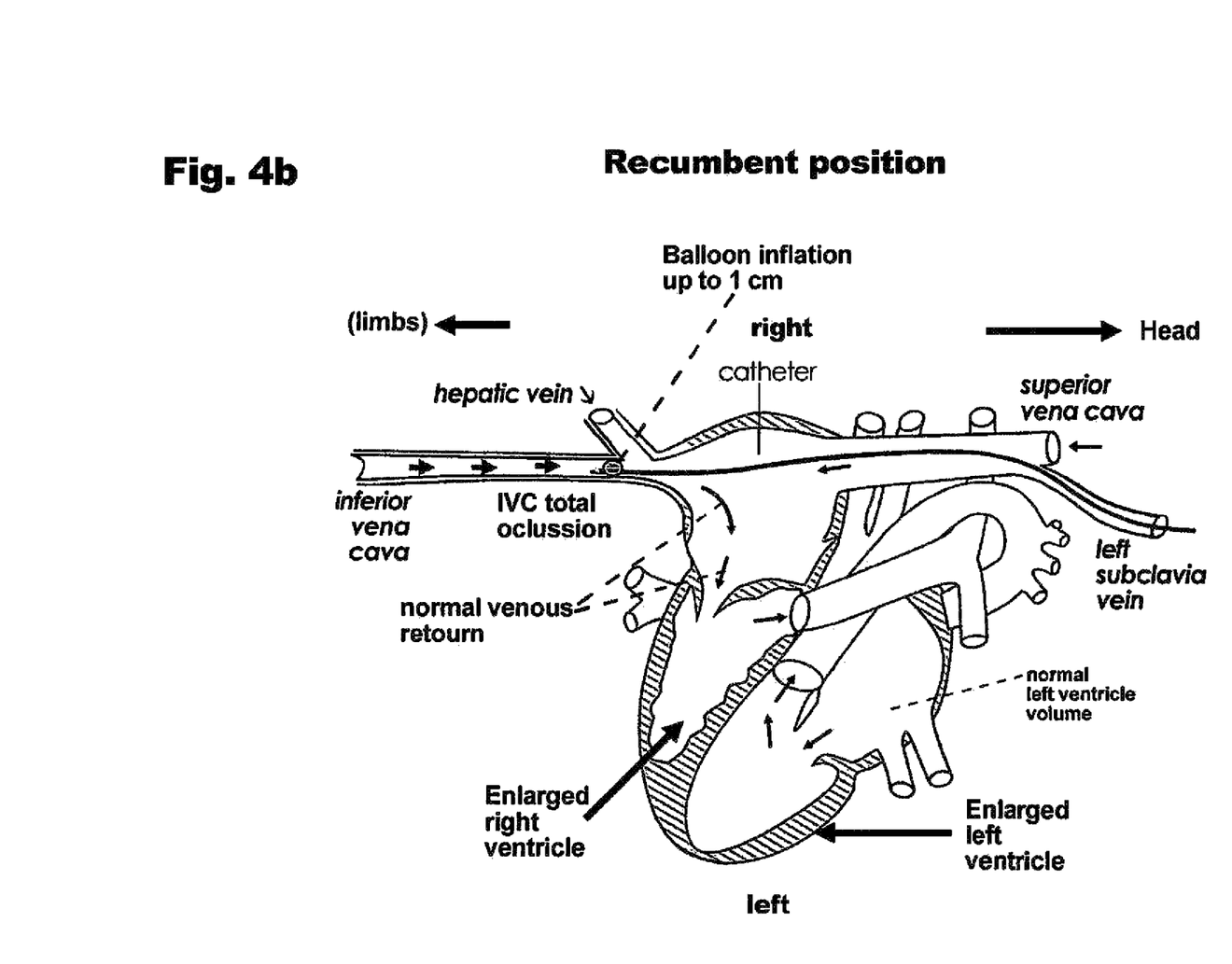
FIG. 4b is a complementary view of FIG. 4a that includes the human heart in the initial phase of treatment (dilated heart).

It can be observed in FIG. 4a how the balloon (5) operates (diameter=1 cm) during the inspiration phase. The collapsing or reduction of the diameter of the inferior vena cava (1 cm) now reaches the same diameter of the balloon, producing total occlusion of the vessel (which is the intended purpose) for an approximate time of 1 second (duration of the inspiratory collapse.) After this period, the inferior vena cava returns to its expiration phase, allowing blood flow again, as illustrated in FIGS. 3a and 4a; therefore, the venous return decreases due to the instant reduction of the flow, thereby decreasing the filling pressure at the right and left ventricles, which effects were previously explained. FIG. 4b is a view of the complete device including the anatomy of the human heart in the initial phase of the treatment in which a dilated heart with hart failure is shown.

Figure 5:
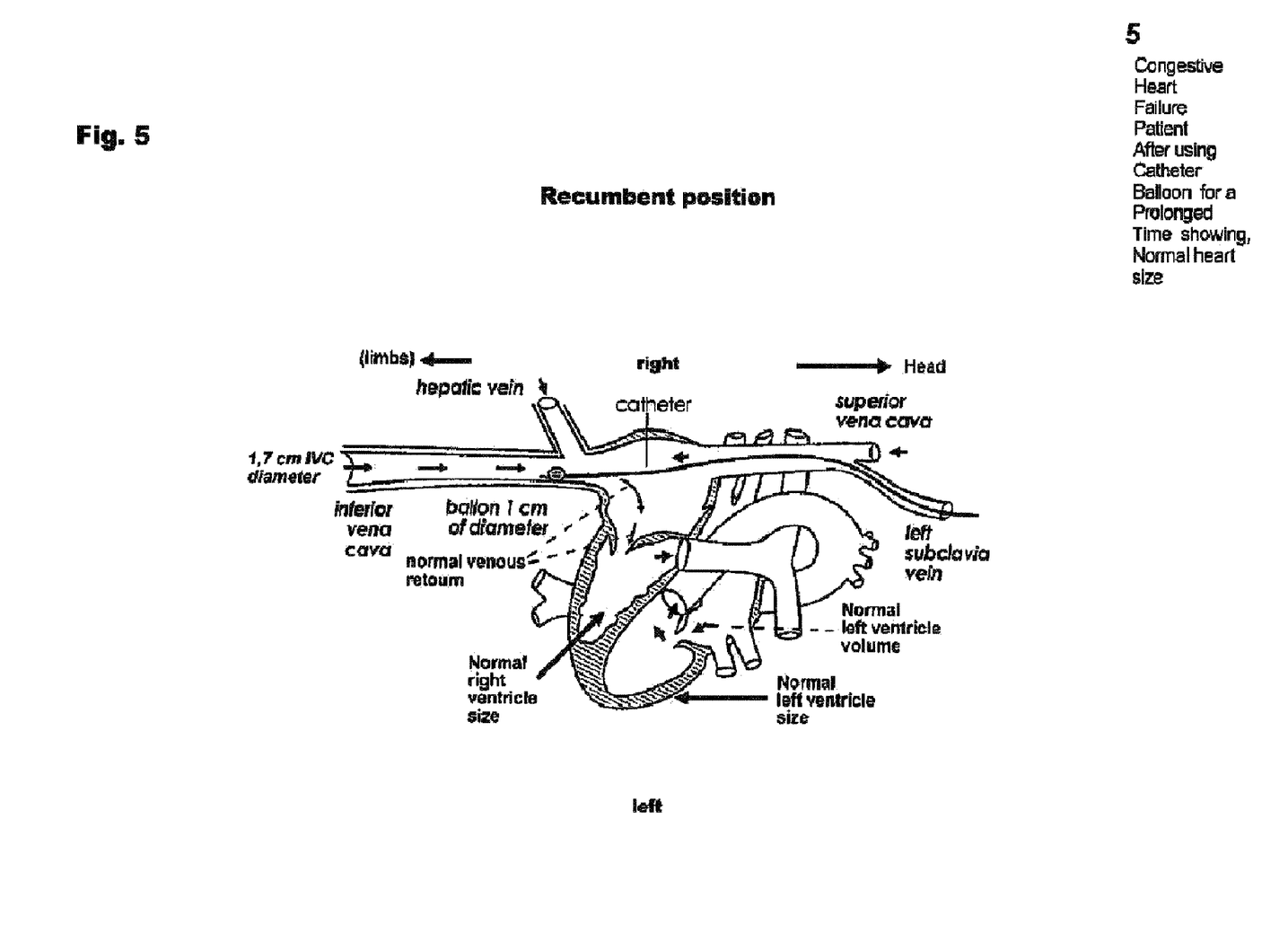
FIG. 5 is a view of the device implanted in the human heart in the final phase of treatment, which shows that the heart reduces its size, which indicates the correction of the heart failure (normal size heart).

FIG. 5 shows the complete device, including the anatomy of the heart at the end of the treatment, which shows a reduction in heart size, after a period three months, at least, when the characteristic symptoms of the heart failure improve.

While preferred embodiments of the invention have been shown and described, various modifications and substitutions may be made thereto without departing from the spirit and scope of the invention. Other variations and modifications may suggest themselves to a person skilled in the relevant arts.

Accordingly, it is to be understood that the present invention has been described by way of illustration only, and this description should not be construed as limiting to the several claims appended hereto.

What is claimed is:

1. A method for treating a heart that has failed by regulation of the venous return, the method comprising:
    introducing into the heart a two-way catheter having an inflatable balloon detachably disposed at a distal end of the catheter and wherein the inflatable balloon is configured to remain expanded once detached from the distal end of the catheter;
    anchoring the inflatable balloon to a blood vessel, wherein the blood vessel is an inferior vena cava;
    inflating the balloon;
    detaching the inflated balloon from the distal end of the catheter, wherein the inflated balloon is configured to remain attached to the blood vessel.

2. The method of claim 1, wherein the balloon is inflated up to substantially half the diameter of an inferior vena cava in expiration.

3. The method of claim 2, wherein the balloon has an external surface comprising one or more slots distributed longitudinally about an axis.

4. The method of claim 1, wherein the balloon is inflated to substantially the diameter of an inferior vena cava in inspiration.

5. The method of claim 4, wherein the balloon has an external surface comprising one or more slots distributed longitudinally about an axis.

6. The method of claim 1, wherein the introducing comprises a puncture in a left subclavian vein of the heart.

7. The method of claim 6, further comprising:
    after the introduction via puncture, the distal end of the two-way catheter is first moved through a right atrium of the heart; and
    after the two-way catheter is moved through the right atrium of the heart, the distal end of the two-way catheter is further moved to a cava-diaphragm junction of the heart.

8. The method of claim 7, further comprising moving the two-way catheter beyond a drainage point of a hepatic vein of the heart.

9. A method, comprising:
    inserting into a heart a two-way catheter comprising a detachable inflatable balloon percutaneously;
    moving the inflatable balloon to a cava-diaphragm junction of the heart via a right atrium;
    anchoring the inflatable balloon at the cava-diaphragm junction;
    inflating said balloon; and
    detaching said inflated balloon from said two-way catheter, wherein the inflated balloon is configured to remain attached at the cava-diaphragm junction.

10. The method of claim 9, wherein said balloon includes an anchoring element, the method further comprising:
    anchoring said balloon to a blood vessel.

11. The method of claim 10, wherein the blood vessel is an inferior vena cava.

12. The method of claim 9 further comprising:
    inflating the balloon to a diameter that is substantially equal to the diameter of an inferior vena cava during inspiration.

13. The method of claim 12, wherein the balloon has an external surface comprising one or more slots distributed longitudinally about an axis.

14. The method of claim 9 further comprising:
    inflating the balloon to a diameter that is up to substantially half the diameter of an inferior vena cava in expiration.

15. The method of claim 14, wherein the balloon has an external surface comprising one or more slots distributed longitudinally about an axis.

16. The method of claim 9 further comprising:
    deflating the balloon for removal.

* * * * *